(12) United States Patent
Gaisford

(10) Patent No.: US 6,182,504 B1
(45) Date of Patent: Feb. 6, 2001

(54) EMULSION COMPOSITION MONITOR

(75) Inventor: Gregory Scott Gaisford, Denver, CO (US)

(73) Assignee: Roxar, Inc., Houston, TX (US)

(*) Notice: Under 35 U.S.C. 154(b), the term of this patent shall be extended for 0 days.

(21) Appl. No.: 09/024,677

(22) Filed: Feb. 17, 1998

Related U.S. Application Data

(60) Provisional application No. 60/064,680, filed on Nov. 3, 1997.

(51) Int. Cl.$^7$ .............................. G01N 33/20; G01F 1/74; G01R 27/04
(52) U.S. Cl. ...................... 73/61.43; 73/861.04; 324/634
(58) Field of Search ................... 73/61.43, 61.44, 73/61.45, 861.04; 324/634, 640, 643, 664, 694, 696, 698

(56) References Cited

U.S. PATENT DOCUMENTS

| | | | |
|---|---|---|---|
| 3,006,189 | 10/1961 | Warren et al. | 73/194 |
| 3,368,147 | 2/1968 | Graham | 324/61 |
| 3,523,245 | 8/1970 | Love et al. | 324/61 |
| 4,266,425 | 5/1981 | Allport | 73/61 R |
| 4,289,020 | 9/1981 | Paap | 73/61.1 R |
| 4,301,400 | 11/1981 | Paap | 324/58.5 A |
| 4,367,440 | 1/1983 | Mazzagatti | 324/445 |
| 4,429,273 | 1/1984 | Mazzagatti | 324/61 R |
| 4,458,524 | 7/1984 | Meador et al. | 73/61.1 R |
| 4,499,418 | 2/1985 | Helms et al. | 324/58.5 A |
| 4,774,680 | 9/1988 | Agar | 364/550 |
| 5,101,367 | 3/1992 | Agar | 364/551.01 |
| 5,103,181 | * 4/1992 | Gaisford et al. | 324/637 |
| 5,263,363 | 11/1993 | Agar | 73/61.44 |
| 5,272,444 | 12/1993 | Cox | 324/698 |
| 5,503,004 | 4/1996 | Agar | 73/61.44 |
| 5,612,490 | * 3/1997 | Carlson | 73/61.43 |

FOREIGN PATENT DOCUMENTS

| | | | |
|---|---|---|---|
| 0268399 | 5/1988 | (EP) | G01N/22/00 |

OTHER PUBLICATIONS

"Complex Microwave Dielectric Properties of Liquids, Solution, and Emulsions" Perl, Jeffery P., Dissertation, May 1984.

"Measurement of Water Content in Oil With Microwave Reflection" Chen, Shilian, Physics Laboratory East China Petroleum Institute.

"Three–Component Flow Measurement in Oil/Gas/Water Mixtures Using Capacitance Transducers" Hammer, E.A., Thesis submitted to University of Manchester.

"Concentration Measurements in Emulsions" Mansour, N.A., Research Scientist, Coal Research Laboratories, Energy Mines and Resources Canada, CANMET, Alberta, Canada.

* cited by examiner

Primary Examiner—Hezron Williams
Assistant Examiner—Jay L. Politzer
(74) Attorney, Agent, or Firm—Dorr, Carson, Sloan & Birney, P.C.

(57) ABSTRACT

A system monitors the composition of emulsions (e.g., oil/water mixtures) by measuring one or more electrical properties (e.g., dielectric constant) of the emulsion. A computer processor determines a plurality of possible solutions using a predetermined relationship between the measured electrical properties and the component fractions of the emulsion. One possible solution is determined for each component that might be the continuous phase in the emulsion. The computer processor then evaluates the component fractions resulting from each possible solution to choose which single solution is most reasonable based on known physical limits for a continuous phase emulsion involving the component associated with each possible solution. The component fractions associated with the selected solution are output by the processor.

24 Claims, 3 Drawing Sheets

EMULSION COMPOSITION MONITOR

RELATED APPLICATION

The present application is based on the Applicant's U.S. Provisional Patent Application Ser. No. 60/064,680, entitled "Emulsion Composition Monitor," filed on Nov. 3, 1997.

BACKGROUND OF THE INVENTION

1. Field of the Invention.

This invention generally relates to the field of monitoring devices used to measure the composition of emulsions and particularly for using electrical measurements to determine the water content of water and oil emulsions.

2. Background of the Invention

The measurement of water content in emulsions is an important one in a number of process monitoring and control applications. Food processing applications include the measurement of the water content of butter, ice cream, and milk. Similarly, the cosmetic industry uses such measurements to control the production of water-laden facial creams.

The measurement of emulsion water content is particularly important in the oil industry. Most oil wells produce significant amounts of water along with the oil. This water tends to be corrosive and deleterious to processing equipment. Water is expensive to transport, difficult to dispose of; and, unlike oil, it has no value. For these reasons, it is important for oil producers, pipeline companies, and refiners to carefully monitor the water content of crude oil.

Many devices based on electrical measurements have been proposed and are being used for determining the water content of oil/water mixtures. Most of the prior art devices have significant limitations. These limitations tend to be caused by the challenging electrical properties of oil/water emulsions. Oil and water emulsions have two distinct forms. In one form, the oil is the continuous phase of the mixture and water is dispersed in the oil as droplets. In the second form, water is the continuous phase and oil is dispersed as droplets within it. The electrical properties of these two forms are quite different even if the water content is identical. The result is that many existing devices operate over a limited range of water content because they cannot measure the electrical properties of both emulsion types. Other devices do not distinguish the emulsion type properly in determining the water content resulting in poor accuracy. Still others attempt to determine the emulsion type so as to accurately determine water content from 0–100%, but do so with methods that are not applicable over the entire range of applications.

The most commonly used measurement devices for these applications are capacitance devices that measure the dielectric constant of the mixture to determine water content. Examples of capacitance devices are disclosed in U.S. Pat. No. 4,266,425 to Allport et al., U.S. Pat. No. 3,523,245 to Love et al., U.S. Pat. No. 3,368,147 to Graham, and U.S. Pat. No. 3,006,189 to Warren et al. These devices generally operate only at lower water contents where oil is the continuous phase of the emulsion because they do not function when the mixture is quite conductive. Another type of device that operates only in the oil continuous phase is disclosed in U.S. Pat. No. 4,458,524 to Meador et al.

An example of a device which only works when the oil/water mixture is water continuous is disclosed in U.S. Pat. No. 4,367,440 to Mazzagatti. The disclosed device measures mixture conductivity to determine water content. This method only works when the mixture is sufficiently conductive to perform a reasonable measurement (i.e., when the water is salty and the mixture is water continuous).

Devices that use electrical measurement methods applicable for both the oil-continuous and water-continuous mixtures are disclosed in U.S. Pat. Nos. 4,289,020 and 4,301,400 to Paap; U.S. Pat. No. 4,429,273 to Mazzagatti; U.S. Pat. No. 4,499,418 to Helms et al.; U.S. Pat. No. 5,272,444 to Cox; and European Patent Application No. 87309659.8 of Bentley et al. None of these references disclose a method for determining how to distinguish between oil-continuous and water-continuous emulsions. Without determining emulsion type, the potential accuracy of these devices is reduced.

Devices that can measure 0–100% water and that use some method for distinguishing emulsion type are disclosed in U.S. Pat. No. 4,774,680 to Agar; U.S. Pat. No. 5,101,367 to Agar; U.S. Pat. No. 5,263,363 to Agar; and U.S. Pat. No. 5,503,004 to Agar. The Agar patents all rely on the comparison of a measured electrical property of the mixture with a predetermined value to determine if the mixture is oil or water continuous. The value that would typically be used for the comparison is the mixture conductivity or another value closely related to it such as microwave energy absorption or loss factor. If the water in the oil/water mixture is conductive, as it is in many applications, then the conductivity of a water-continuous emulsion will be much higher than the conductivity of an oil-continuous mixture having the same water content. However, if the water is fresh water which has a low conductivity, this method is not a reliable determinant of emulsion type.

The comparison method taught in the Agar patents could also be applied using a dielectric constant comparison to a threshold value to determine emulsion type. However, this method is harder to apply because the difference between the dielectric constant of oil-continuous and water-continuous emulsions is usually not so large as is the conductivity difference and because the relevant dielectric constants are quite temperature dependent.

Perl, "Complex Microwave Dielectric Properties of Liquids, Solutions and Emulsions", Ph.D. thesis, Illinois Institute of Technology (May 1984) discloses a system for determining the percentages of oil and water in an oil/water sample by measuring the resonant frequency and Q of a resonant cavity containing the sample. The measured Q and resonant frequency are in turn related to the real and imaginary parts, e' and e", of the complex dielectric constant, e*. Perl uses the loss factor (e"/e') to determine the emulsion type (i.e., oil-in-water or water-in-oil) and then to determine volume fractions of the sample.

Chen, "Measurement of Water Content in Oil With Microwave Reflection", East China Petrol. Inst. (vol. 7, no. 3, pp. 376–388, 1983) determines the percentages of oil and water in an oil/water sample by measuring the reflection coefficient using a microwave apparatus coupled to a mixture of oil and water flowing in a pipe. The measured reflection coefficient is directly related to the impedance of the oil and water mixture and the impedance of the mixture in turn is directly related to the dielectric constant of the mixture. Chen also measures the resistivity of the flowing mixture using an inductive coil around the pipe to determine the emulsion type.

Mansour, "Concentration Measurements in Emulsions," Presentation at the $22^{nd}$ International Microwave Power Symposium: A Macro View of Microwaves and FR Heatings, Cincinnati, Ohio (Sept. 1987) discloses a system that measures one or more electrical properties of oil/water mixtures, determines from the measured properties if the mixture is oil or water continuous, and determines the water content of the mixture using two different curves (one each for oil and water continuous mixtures) relating the measured electrical properties to water content. Mansour describes storing the different curves in a computer in the form of equations. Finally, Mansour states the need for temperature correction to compensate the measurements for changes that occur as a function of temperature.

Hammer, "Three-Component Flow Measurement in Oil/Gas/Water Mixtures Using Capacitance Transducers", Ph.D. thesis, University of Manchester, Manchester, UK (Dec. 1983) describes a system consisting of: (1) a microcomputer containing equations for oil and water continuous mixtures; (2) a capacitance transducer that measures electrical properties (capacitance and resistance or conductance) of the mixture; (3) a temperature transducer; (4) a flow measuring device; and (5) a display. The system calculates the water content from the measured electrical properties (suitably corrected for temperature), measures the flow rate, and displays the results on a display. In each case, there is a distinct jump when the mixture changes from oil to water continuous, which permits the emulsion type to be determined.

3. Solution to the Problem

To enable emulsion composition monitors utilizing measurements of an electrical property of the mixture to determine composition in a wider range of applications, a simpler and more generally useful method for determining emulsion type is needed. The present invention takes advantage of the limited range of water contents at which both oil-continuous and water-continuous emulsions can exist.

In typical oil field applications, oil-continuous emulsions rarely contain more than 75% water and water-continuous emulsions rarely contain less than 35% water. These represent the extremes. For a given combination of oil and water, the typical overlap in water contents at which the mixture can be either oil-continuous or water-continuous is far less—usually 5% to 15%. Thus for example, if the highest sustainable water content in an oil-continuous mixture is 65%, then the lowest sustainable water content in a water-continuous emulsion is about 50% water.

The prior art includes a number of mathematical relationships between the electrical properties and the component content of emulsions. These mathematical relations give different solutions for oil-continuous and water-continuous emulsions. When calculating the water content from a measured electrical property using such relations, there is a large difference between the result for the oil-continuous and water-continuous results. The difference is much larger than is the range over which the two emulsion types can coexist for a given oil/water mixture. Suppose the calculated oil-continuous result is 65% water and this represents the maximum possible oil-continuous water content. The water-continuous solution calculated from the same measured dielectric constant will be approximately 39%. This is well below the water content at which a water-continuous emulsion could exist. In other words, the oil-continuous solution gives a realistic value, but the water continuous result does not. Thus, it is possible to determine the emulsion type simply by comparing the water contents associated with the oil and water continuous solutions and selecting the most reasonable solution of the two. This approach to determining emulsion type makes it possible to accurately measure water content from 0–100% using devices that measure emulsion electrical properties.

Oil/water mixtures are only one example. The present invention could be used to determine the composition of any emulsion in which the electrical properties of the emulsion differ significantly depending on which of the components is the continuous phase of the mixture.

The present invention could also be utilized with mixtures containing more than two components. For these mixtures too, there are two different composition solutions depending on the emulsion type for the components that make up an emulsion. An example of such an application is multiphase metering in the oil industry. Multiphase meters measure, among other things, the composition of oil, water and gas emulsions. Accurate measurement of these three components is dependent on the determination of the oil/water emulsion type as it is for an oil/water mixture containing no gas. Thus, it should be understood by those skilled in the art that the method and apparatus taught herein could be used within a multicomponent composition monitor such as that taught in U.S. Pat. No. 5,103,181 to Gaisford which discloses a system for measuring electrical properties and temperature.

SUMMARY OF THE INVENTION

The present invention provides a system for monitoring the composition of emulsions, such as oil/water mixtures. One or more electrical properties (e.g., dielectric constant) of the emulsion are measured. A computer processor determines a plurality of possible solutions using a predetermined relationship between the measured electrical properties and the component fractions of the emulsion. One possible solution is determined for each component that might be the continuous phase in the emulsion. The processor then evaluates the component fractions resulting from each possible solution to choose which single solution is most reasonable based on known physical limits for a continuous phase emulsion involving the component associated with each possible solution. The component fractions associated with the selected solution are output by the processor.

BRIEF DESCRIPTION OF THE DRAWINGS

The present invention can be more readily understood in conjunction with the accompanying drawings, in which:

FIG. 1 also illustrates a typical range in which both emulsion types can exist.

DETAILED DESCRIPTION OF THE INVENTION

Many mathematical relations describe the electrical properties of emulsions as a function of component content. One such relation is the Bruggeman equation relating emulsion dielectric constant to composition. This equation will be used to demonstrate the method and apparatus. Many other equations including the equations of Wiener, Böttcher, or Kubo-Nakamura or empirical relations, or even look-up tables could be used for the present method. It should be understood that the present invention can be applied with other relations than the Bruggeman equation and with other electrical properties than dielectric constant.

The Bruggeman equation is shown below:

$$\left(\frac{\varepsilon - \varepsilon_p}{\varepsilon_m - \varepsilon_p}\right)\left(\frac{\varepsilon_m}{\varepsilon}\right)^{\frac{1}{3}} = 1 - \Phi_p$$

where:
∈=dielectric constant
Φ=volume fraction
m=continuous phase
p=disperse phase Applied to water continuous emulsions of oil and water mixtures, the equation is:

$$\left(\frac{\varepsilon - \varepsilon_o}{\varepsilon_w - \varepsilon_o}\right)\left(\frac{\varepsilon_w}{\varepsilon}\right)^{\frac{1}{3}} = \Phi_w$$

where:
o=oil
w=water

Similarly for oil continuous emulsions:

$$\left(\frac{\varepsilon - \varepsilon_w}{\varepsilon_o - \varepsilon_w}\right)\left(\frac{\varepsilon_o}{\varepsilon}\right)^{\frac{1}{3}} = 1 - \Phi_w$$

Figure 1:
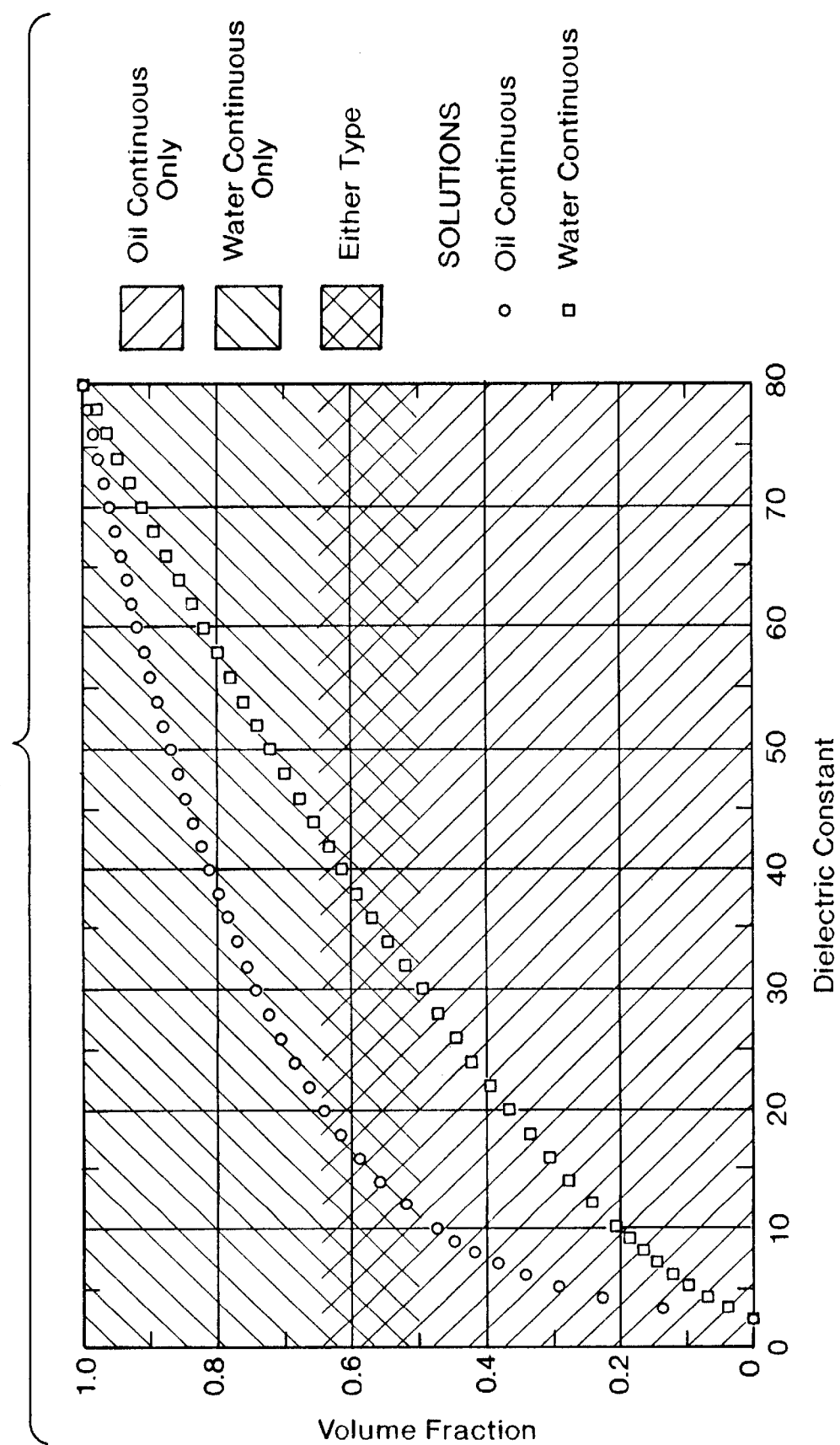
FIG. 1 is a graph showing the dielectric constant versus water content for oil-continuous and water-continuous emulsions, respectively.

Typical values for $\varepsilon_o$ and $\varepsilon_w$ are 2 and 80, respectively. FIG. 1 shows the a graph of the volume fraction $\Phi_w$ as a function of mixture dielectric ∈. Table 1 shows the actual values. Note that o(w) refers to an oil-continuous emulsion and w(o) to a water-continuous emulsion. As the figure illustrates, two different solutions are possible for a given dielectric constant measured for the mixture. The emulsion type must be determined in order to know which solution is the correct one.

FIG. 1 also illustrates a typical span of water contents over which both emulsion types can exist. The span shown in FIG. 1 is 15% ranging from 50 to 65% water. The actual water contents at which the emulsion types can coexist may vary toward higher water content (approximately 60–75%) or toward lower water contents (35–50%) However, the span of water contents at which both emulsion types can exist is typically 5–15%.

Utilizing the Bruggeman equation, the method for determining the emulsion type calls for calculating the water content from the measured mixture dielectric constant for both the oil-continuous and the water-continuous cases, then rejecting the solution that is physically unrealistic. The method can be implemented by comparing the oil-continuous solution to an upper threshold water content at which oil-continuous mixtures exist. If the solution is less than the threshold, then the oil-continuous solution is used. If not, the water-continuous solution is used. For, the oil/water mixture shown in FIG. 1, an appropriate threshold level would be 0.70 or 70% water. This is 5% higher than would normally be expected, but will accommodate anomalous mixtures. Using a threshold value several percent above the actual upper limit will not result in erroneous emulsion type determination. If a higher than expected oil-continuous water content, say 68%, is encountered, it will not be incorrectly identified as water continuous. On the other hand, no realistic water-continuous dielectric constant will give an oil continuous solution below the elevated threshold either. This is one of the strengths of the method.

From FIG. 1, it is clear that solutions to the equations that lie well outside the range where the particular emulsion type can exist are impossible. For example, an oil-continuous solution of 90% water content is not possible. What is less obvious is that for any given mixture dielectric constant, only one of the solutions gives a reasonable result. The other is usually much lower or much higher than is likely to occur under natural conditions. Table 1 shows numerically some of the values used to generate FIG. 1 and helps illustrate why the present method works.

Example 1. The mixture dielectric constant is measured to be 4.5. Referring to Table 1, the corresponding oil-continous and water-continuous water contents are 26.1% and 8.4% respectively. The oil-continuous solution of 26.1% is less than the threshold value of 70%; therefore, the mixture is determined to be oil continuous and the water content is 26.1%.

Example 2. The mixture dielectric constant is measured to be 14.0. The corresponding oil-continuous and water-continuous water content solutions are 55.8% and 27.5% respectively. The oil-continuous solution of 55.8% is less than the threshold value of 70%. Therefore, the mixture is determined to be oil continuous and the water content is 27.5%. The water-continuous solution is well below the range of water contents at which a water-continuous mixture could realistically occur.

Example 3. The mixture dielectric constant is measured to be 22.0. The corresponding oil-continuous and water-continuous water contents are 66.6% and 39.4% respectively. The oil-continuous solution of 66.6% is less than the threshold value of 70%. Therefore, the mixture is determined to be oil continuous and the water content is 66.6%. Even though the oil-continuous solution is near its upper limit, the water-continuous solution of 39.4% is still well below its limit.

Example 4. The mixture dielectric constant is measured to be 33.0. The corresponding oil-continuous and water-continuous water contents are 76.3% and 53.4% respectively. The oil-continuous solution of 76.3% is greater than the threshold value of 70%. Therefore, the mixture is determined to be water continuous and the water content is 53.4%.

Example 5. The mixture dielectric constant is measured to be 45.0. The corresponding oil-continuous and water-continuous water contents are 84.1% and 60.3% respectively. The oil continuous solution of 84.1% is greater than the threshold value of 70%. Therefore, the mixture is determined to be water continuous and the water content is 60.3%.

For each example, comparing the oil continuous result to an upper threshold gives an emulsion type and water content consistent with the limits shown in FIG. 1. An equivalent method uses a low water content threshold for water-continuous emulsions. For the oil and water mixture illustrated in FIG. 1, the low end limit would be approximately 48% water. The same result is achieved in each example if the water-continuous result is compared to this low threshold. If it is higher, the mixture is water continuous.

The threshold water content used to implement this method is not a constant for all applications and all oil and water combinations. The specific chemistry of the components will affect the threshold value. Thus, the threshold value must be appropriately set for a given device to prevent unnecessary errors.

The electrical properties of oil and water are not constant. A water content monitor must be appropriately calibrated for the specific oil and water so that these values can be entered into an equation such as the Bruggeman equation to determine the water content from the measured electrical properties. For example, the dielectric constants of oil and water are temperature dependent. If the present method is to be used over a range of temperatures, these dielectric constants must be determined at the measurement temperature so that the values used in the equations or look-up tables result in the correct water content determination. The Bruggeman equation becomes the following when the temperature dependence is accounted for:

$$\left(\frac{\varepsilon - \varepsilon_p(T)}{\varepsilon_m(T) - \varepsilon_p(T)}\right)\left(\frac{\varepsilon_m(T)}{\varepsilon}\right)^{\frac{1}{3}} = 1 - \Phi_p$$

where T=temperature.

Figure 2:
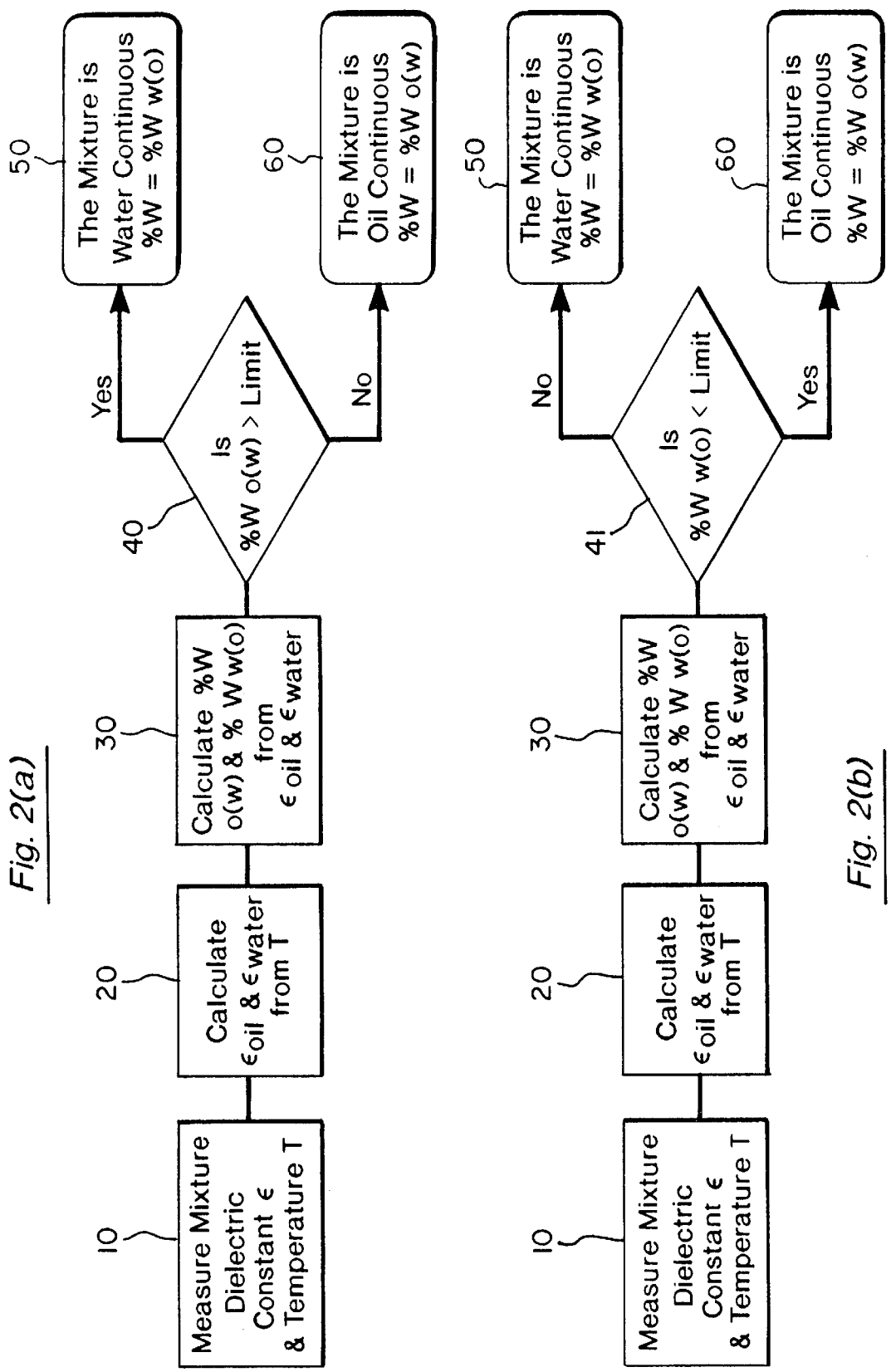
FIGS. 2($a$) and 2($b$) are simplified flowcharts illustrating two implementations of the present invention for measuring emulsion type and water content.

FIGS. 2(a) and 2(b) are simplified flowcharts of two implementations of the present method as applied to oil and water mixtures and dielectric constant measurements. FIG. 2(a) is the present method applied with an oil-continuous, high-water-content threshold limit. FIG. 2(b) is the present method applied with a water-continuous, low-water-content threshold limit.

With reference to FIG. 2(a), an emulsion's dielectric constant, ($\in$) and temperature (T) are measured in step 10. In step 20, the dielectric constants of oil ($\in_{oil}$) and water ($\in_{water}$) are determined at temperature T. In step 30, the two different water content (% W) solutions corresponding to oil-continuous, o(w), and water-continuous, w(o), emulsions are determined from $\in$, $\in_{oil}$, and $\in_{water}$. Step 40 determines whether oil or water is the continuous phase by comparing the oil-continuous percent water, % W o(w), to an upper threshold limit. If it is greater, the mixture is determined to be water continuous and the percent water is set to the water-continuous solution, % W w(o), in step 50. If it is less than the limit, the mixture is determined to be oil continuous and the percent water is set to the oil-continuous solution, % W o(w), in step 60.

With reference to FIG. 2(b), steps 10, 20, and 30 are identical to the like-numbered steps in FIG. 2(a). However, step 41 determines whether oil or water is the continuous phase by comparing the water continuous percent water, % W w(o), to a lower threshold limit. If it is less, the mixture is determined to be oil continuous and the percent water is set to the oil continuous solution, % W o(w), in step 60. If it is greater than the limit, the mixture is determined to be water continuous and the percent water is set to the water continuous solution, % W w(o), in step 50.

The methods illustrated in FIGS. 2(a) and 2(b) are readily translatable to any mixture with two or more components where two of the components form an emulsion and for which the dielectric constant of those two components are significantly different from one another, as with oil and water. In such a case, the composition solution determined from the dielectric constant will be different for the mixture depending on which phase is the continuous phase of the two component emulsion. Either of the two related methods shown in FIGS. 2(a) and 2(b) can be used to determine which phase of the emulsion is the continuous phase and therefore which of the composition solutions is the correct one. Furthermore, it should be clear to one skilled in the art that the method illustrated in FIGS. 2(a) and 2(b) utilizing the dielectric constant could be similarly applied with other electrical properties, such as conductivity, loss factor, admittance, impedance, microwave absorption, etc.

Figure 3:
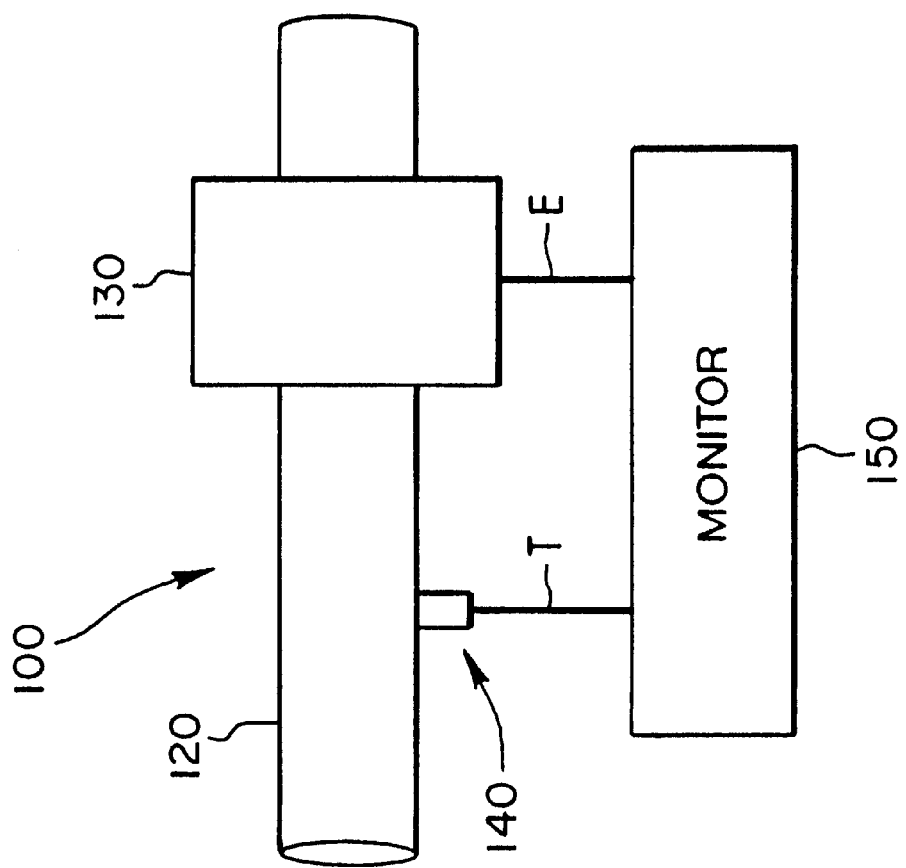
FIG. 3 is a block diagram of an emulsion composition monitor in accordance with the present invention.

With reference to FIG. 3, a production stream consisting of an emulsion of components 1 and 2 having different electrical properties (i.e. oil and water) flows through the emulsion composition monitor designated 100. The emulsion composition monitor 100 includes a conduit 120 through which the mixture passes. The mixture to be measured may be conducted through conduit 120 on a continuous basis and conduit 120 may comprise part of a mixture transmission pipeline. The emulsion composition monitor 100 includes a measurement means 130 for measuring one or more electrical properties (E) of the mixture. The measurement means 130 may be any of a variety of devices for measuring the electrical properties of the flowing mixture such as a microwave device, an admittance measuring device, or a suitably designed capacitance device. A temperature sensor 140 measures the temperature (T) of the mixture.

The measurement means 130 and temperature sensor 140 are connected to a computer processor 150 and provide signals corresponding to the measured E and T values. The processor 150 determines the individual electrical properties of components 1 and 2, respectively, at temperature T. These values in turn are used together with the measured electrical properties, E, to determine the percent of component 2 for:

(a) an emulsion with component 1 as the continuous phase (i.e. oil continuous) (designated solution 1); and (b) an emulsion with component 2 as the continuous phase (i.e. water continuous) (designated solution 2).

The two solutions can be found using a known analytical relationship such as the Bruggeman equation, an empirically derived equation, from look-up tables, or from a combination of these.

The processor 150 can use either of two related methods illustrated in FIGS. 2(a) and 2(b) to determine whether component 1 or 2 is the continuous phase of the mixture and therefore determine which solution is correct. Using the first method shown in FIG. 2(a), solution 1 is compared to a predetermined upper limit threshold value. If solution 1 is greater than the threshold value, the processor 150 determines that component 2 is the continuous phase and outputs a composition value corresponding to solution 2. If, on the other hand, solution 1 is less than the threshold value, the processor 150 determines that component 1 is the continuous phase and outputs a composition value corresponding to solution 1.

Using the second method shown in FIG. 2(b), solution 2 is compared to a predetermined lower limit threshold value. If solution 2 is less than the threshold value, the processor 150 determines that component 1 is the continuous phase and outputs a composition value corresponding to solution 1. If, on the other hand, solution 2 is greater than the threshold value, the processor 150 determines that component 2 is the continuous phase and outputs a composition value corresponding to solution 2.

Numerous variations and modifications can be made without departing from the invention. For example, many types of temperature sensors and electrical property measurement means could be used as components of the emulsion composition monitor. Moreover, the design of the processor 150 could take many forms. Different combinations of analog-to-digital converters, digital-to-analog converters, comparators, look-up tables, microprocessors, etc. could be used to determine the emulsion type and composition.

The present invention can be applied to the composition measurement of mixtures containing more than two components where at least two of the components form an emulsion and where the same two components have significantly different electrical properties. In the case of such multicomponent mixtures, there will be two different composition solutions just as with simpler two component mixtures.

The above disclosure sets forth a number of embodiments of the present invention. Other arrangements or embodiments, not precisely set forth, could be practiced under the teachings of the present invention and as set forth in the following claims.

TABLE 1

| Dielectric Constant | % W o(w) | % W w(o) | Difference |
|---|---|---|---|
| 2.0 | 0.0 | 0.0 | 0.0 |
| 3.0 | 13.8 | 3.8 | 9.9 |
| 4.5 | 26.1 | 8.4 | 17.8 |
| 6.0 | 34.2 | 12.2 | 22.1 |
| 8.0 | 41.8 | 16.6 | 25.3 |
| 10.5 | 48.7 | 21.4 | 27.3 |
| 14.0 | 55.8 | 27.5 | 28.3 |
| 18.0 | 61.8 | 33.7 | 28.1 |
| 22.0 | 66.6 | 39.4 | 27.1 |
| 33.0 | 76.3 | 53.4 | 22.9 |
| 39.0 | 80.5 | 60.3 | 20.2 |
| 45.0 | 84.1 | 66.8 | 17.3 |
| 52.0 | 87.9 | 74.0 | 13.9 |
| 62.0 | 92.7 | 83.7 | 8.9 |
| 80.0 | 100.0 | 100.0 | 0.0 |

I claim:

1. A method for determining the composition of an emulsion having a plurality of components, wherein an unknown one of said components constitutes the continuous phase in the emulsion, said method comprising:
measuring at least one electrical property of the emulsion;
solving a predetermined mathematical relationship between the measured electrical properties and the component fractions of the emulsion to determine a plurality of possible solutions, wherein one possible solution is determined for each component that might be the continuous phase in the emulsion;
selecting one of said possible solutions by comparing the component fractions resulting from each of said possible solutions to physical limits for a continuous phase emulsion of the component associated with the possible solution; and
outputting the component fractions associated with the selected solution.

2. The method of claim 1 wherein said electrical properties comprise the dielectric constant of the emulsion.

3. The method of claim 1 wherein said electrical properties comprise the conductivity of the emulsion.

4. The method of claim 1 wherein said electrical properties comprise the loss factor of the emulsion.

5. The method of claim 1 wherein said electrical properties comprise the admittance of the emulsion.

6. The method of claim 1 wherein said electrical properties comprise the impedance of the emulsion.

7. The method of claim 1 wherein said electrical properties comprise the microwave absorption of the emulsion.

8. The method of claim 1 wherein said emulsion is an oil/water mixture.

9. The method of claim 1 wherein said mathematical relationship comprises the Bruggeman equation.

10. The method of claim 1 further comprising measuring the temperature of the emulsion, and wherein said mathematical relationship is dependent on said temperature.

11. The method of claim 1 wherein said step of selecting one of said possible solutions comprises comparing the component fraction of the continuous component for the possible solution against a predetermined lower limit.

12. The method of claim 1 wherein said step of selecting one of said possible solutions comprises comparing the component fraction of one of the non-continuous components for the possible solution against a predetermined upper limit.

13. A monitor for determining the composition of an emulsion having a plurality of components, wherein an unknown one of said components constitutes the continuous phase in the emulsion, said monitor comprising:
means for measuring at least one electrical property of the emulsion;
means for determining a plurality of possible solutions using a mathematical relationship between said measured electrical properties and the component fractions of the emulsion, wherein one possible solution is determined for each component that might be the continuous phase in the emulsion;
means for evaluating the component fractions resulting from each possible solution to select one possible solution based on physical limits for a continuous phase emulsion involving the component associated with each possible solution; and
means for outputting the component fractions associated with the selected solution.

14. The emulsion composition monitor of claim 13 wherein said electrical properties comprise the dielectric constant of the emulsion.

15. The emulsion composition monitor of claim 13 wherein said electrical properties comprise the conductivity of the emulsion.

16. The emulsion composition monitor of claim 13 wherein said electrical properties comprise the loss factor of the emulsion.

17. The emulsion composition monitor of claim 13 wherein said electrical properties comprise the admittance of the emulsion.

18. The emulsion composition monitor of claim 13 wherein said electrical properties comprise the impedance of the emulsion.

19. The emulsion composition monitor of claim 13 wherein said electrical properties comprise the microwave absorption of the emulsion.

20. The emulsion composition monitor of claim 13 wherein said emulsion comprises an oil/water mixture.

21. The emulsion composition monitor of claim 13 wherein said mathematical relationship comprises the Bruggeman equation.

22. The emulsion composition monitor of claim 13 further comprising means for measuring the temperature of the emulsion, and wherein said mathematical relationship is dependent on said temperature.

23. The emulsion composition monitor of claim 13 wherein said means for evaluating compares the component fraction of the continuous component for each possible solution against a predetermined lower limit.

24. The emulsion composition monitor of claim 13 wherein said means for evaluating compares the component fraction of one of the non-continuous components for each possible solution against a predetermined upper limit.

* * * * *